United States Patent [19]

Brooks

[11] 4,203,434
[45] May 20, 1980

[54] TIMING ASSEMBLY FOR OXYGEN RESPIRATION UNITS

[76] Inventor: Lula M. Brooks, 5038 N. Kenmore, Chicago, Ill. 60640

[21] Appl. No.: 893,901

[22] Filed: Apr. 5, 1978

[51] Int. Cl.$^2$ .......................................... A61M 16/00
[52] U.S. Cl. ........................ 128/205.24; 137/DIG. 9; 128/205.23
[58] Field of Search .......................... 128/145.5–145.8, 128/142 R, 142.2, 142.3, 142.4, 188, 205, 202, 209, 210, DIG. 17, 2 C, 2 L, 2.08; 137/DIG. 9, 102

[56] References Cited

U.S. PATENT DOCUMENTS

| | | | |
|---|---|---|---|
| 2,483,722 | 10/1949 | Bennett | 137/102 |
| 2,830,580 | 4/1958 | Saklad et al. | 128/DIG. 17 |
| 2,867,210 | 1/1959 | Bennett | 128/145.8 |
| 3,915,164 | 10/1975 | Bird | 128/145.6 X |
| 3,923,055 | 12/1975 | Hammacher | 128/145.8 |

Primary Examiner—Henry J. Recla
Attorney, Agent, or Firm—Howard I. Podell

[57] ABSTRACT

A timing assembly adapted to be secured to the outlet of an oxygen respiration unit which includes a housing having an inlet connected to the outlet of the unit and an outlet connected to a pneumatic valve which is operatively connected to a battery operated timer which shuts off oxygen flow from the unit and automatically admits outside air through an air filter after a preset time.

8 Claims, 4 Drawing Figures

TIMING ASSEMBLY FOR OXYGEN RESPIRATION UNITS

FIELD OF THE INVENTION

This invention relates generally to a timing assembly for an oxygen respirating unit used for administering oxygen.

DESCRIPTION OF THE PRIOR ART

The prior art, as exemplified by U.S. Pat Nos. 3,265,061; 3,871,371; 3,734,091; 3,911,899; 3,952,739 and 3,307,541 is generally illustrative of various devices of this type. While such devices are generally acceptable for their intended purpose they have not proven to be entirely satisfactory in that they are either complex and expensive to manufacture, or bulky and inconvenient to use, or require unusual skill and/or dexterity to operate. As a result of the shortcomings of the prior art, typified by the above, there has developed and continues to exist a substantial need for devices of the character described. Despite this need, and the efforts of many individuals and companies to develop such devices, a satisfactory device meeting this need has heretofore been unavailable.

The principal object of this invention is to provide a device or article of this character which combines simplicity, strength and durability in a high degree, together with inexpensiveness of construction so as to encourage widespread use thereof.

Other objects of this invention will in part be obvious and in part hereinafter pointed out.

The invention accordingly consists in the features of construction, combinations of elements, and arrangement of parts which will be exemplified in the construction hereinafter described, and of which the scope of application will be indicated in the following claims.

SUMMARY OF THE INVENTION

This invention resides in a timing assembly adapted to be secured to the outlet of an oxygen respiration unit which includes a housing having an inlet connected to the outlet of the unit and an outlet connected to a pneumatic valve which is operatively connected to a battery operated timer which shuts off oxygen flow from the unit and automatically admits outside air through an air filter after a preset time.

BRIEF DESCRIPTION OF THE DRAWINGS

In the accompanying drawing, in which is shown one of the various possible illustrative embodiments of this invention, wherein like reference character identify the same or like parts.

DESCRIPTION OF THE PREFERRED EMBODIMENT

Figure 1:
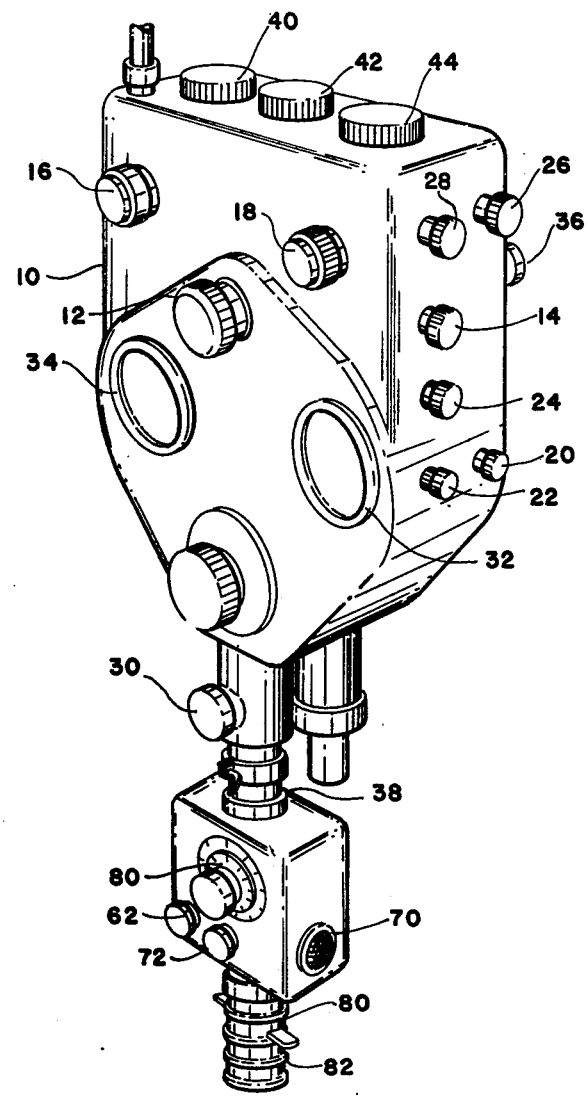
FIG. 1 is an isometric view of a respirator unit provided with a timer according to the invention.

The invention is disclosed with reference to a respirator unit described and claimed in U.S. Pat No. 3,265,061 to the Bennett Respiration Products Company. The unit is further described in the operating instructions manual for the Bennett Model PR-2 Respiration Unit published by the same company, 1639 Eleventh Street, Santa Monica, Calif. 90406.

The Bennett Respirator is used in hospitals, clinics and the like in treating patients who have breathing difficulties, i.e., emphysema, asthema, collapsed lung, pneumonia etc. The prescribed treatment calls for five or ten or fifteen or twenty minutes exposure to the dry oxygen which is forced into the lungs by the respirator. However, it has no timing device. Consequently a nurse, or therapist must be in attendance throughout the treatment period. The unit does not shut off by itself and if the attendant is called away, there is a danger that the patient will receive too much dry oxygen. This excess will at the least cause discomfort and could cause a dangerous drying out condition in the patient's lungs. When the respirator is functioning as as the prescribed time allowance, it allows the lungs to clear themselves of phlegm. The phlegm is loosened by the dry oxygen and is coughed-up by the patient, thereby relieving the patient's distress. Once the phlegm is removed after 5 or 10 or 15 or 20 minutes, the unit should be shut off as over exposure will dehydrate the lungs. This result is similar to a sun lamp in the sense that over exposure can be worse than no exposure at all.

Referring now to the drawings, a respirator unit is designated generally by reference character 10. The unit includes the following elements:

Pressure, control means 12 which sets control pressure and adjustable from 0 to 50 $cmH_2O$.

Dilution, control means 14 which changes oxygen percentage with room air dilution. Adjustable for nominal 100% oxygen or air/oxygen dilution.

Rate, control means 16 sets rate of automatic cycling. Can control start of both inspiration and expiration in automatic cycling. Adjustable from 0 to 70 cycles per minute.

Expiration time, controls 18 modifies setting of the rate control to increase time in expiration.

Nebulization-inspiration, control 20 adjusts flow from the nebulizer during inspiration. Controls medication or humidity in the inspired gas.

Nebulization-expiration, controls 22 adjusts flow from nebulizer during expiration. Controls medication or humidity in manifold and tube for initial inspiratory flow. Maintains pressure at the nebulizer jet so that there is no inspiratory nebulization time lag.

Negative pressure, controls 24 sets negative expiratory pressure. Adjustable from 0 to minus 6 $cmH_2O$.

Sensitivity, controls 26 provides control of unit sensitivity to patient inspiratory effort.

Terminal flow, control 28 which adjusts terminal flow point at which the Bennett Valve closes. Used to compensate for gross system leak or very low flow from the nebulizer, if inspiration is to be pressure-limited. If the unit is set at 100% and if the terminal flow control is open, oxygen percentage will be somewhat less than 100%.

Peak flow, controls 30 adjusts maximum peak flow from the Bennett valve.

Control pressure gauge, 32 indicates pressure which will be reached in the tube system if inspiration is pressure-limited.

System pressure gauge, 34 indicates pressure in the tube system.

A gas inlet 36 from a source of oxygen is mounted on the top of the unit and a gas outlet 38 provided at the bottom.

The three cylinders on top of the unit are part of the automatic cycling mechanism. The pistons are normally in an up position and move down when activated piston 40 limits the length of time in expiration; piston 42 rephases the other pistons and piston 44 limits the length of time in inspiration.

The timer 46 includes housing 48 which has an inlet 50 having a mouth 52 lined with a rubber seal 54 and actuating lever 56 for engaging outlet 38 to allow oxygen into pipe 58.

Figure 2:
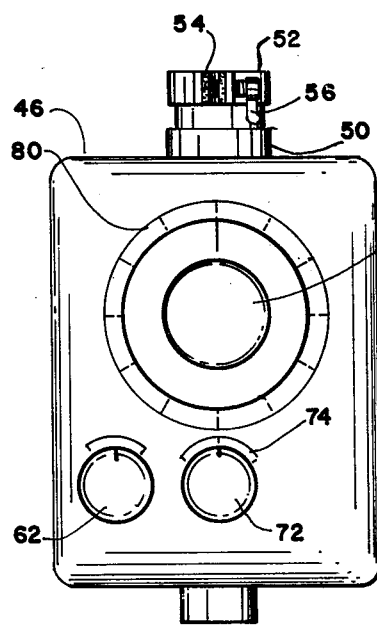
FIG. 2 is front elevation of the timer housing.
Figure 3:
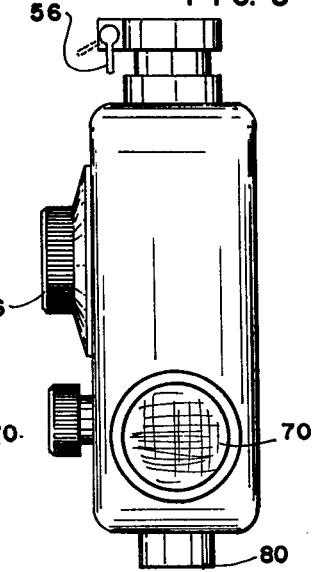
FIG. 3 is a side elevation of same.
Figure 4:
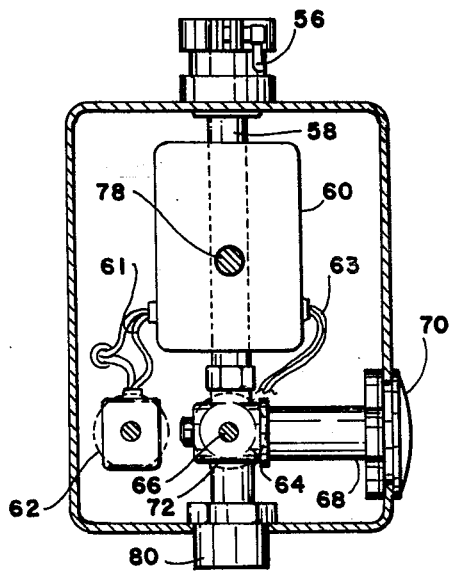
FIG. 4 is a sectional view therethrough.

A battery (not shown) in housing 60 is connected by wires 61 to an ON-OFF switch 62 and to a micromotor (not shown) by wires 63. The D.C. micromotor is mounted in valve housing 64 and has a shaft 66 on which is mounted a rotary valve communicating with oxygen tube 58 and air inlet 68 which is separated from the atmosphere by filter 70. On the outer end of shaft 66 is keyed a knob 72 (FIG. 2) surmounting a dial 74 for manual operation of the valve.

The timer 46 is of conventional construction and includes a knob 76 mounted on a shaft 78 for winding a calibrated spring. The timer can be set for various timing periods as indicated on dial 80. At the expiration of the preset time, the timing mechanism will, in known manner, set off an audible sound and will cause the battery to energize the micromotor to move its shaft 66 so that the pneumatic valve will be moved in known manner from its originally set position (oxygen) to the other (air).

The apparatus has an outlet 80 to which is connected a tube 82 leading to a face mask adapted to be secured on the face of a patient. After applying the mask, dial 72 is set to "Oxygen", timer 76 is turned counterclockwise to the desired time frame of 5, 10 or 15 or 20 minutes and switch 62 is turned on. On completion of the time period, the alarm will sound and valve 64 will be turned by the micromotor to only allow air through inlet 68.

It will thus be seen that there is provided a device in which the several objects of this invention are achieved, and which is well adapted to meet the conditions of practical use. Its advantages are easily seen.

It is thought that persons skilled in the art to which this invention relates will be able to obtain a clear understanding of the invention after considering the foregoing description in connection with the accompanying drawing. Therefore, a more lengthy description is deemed unnecessary.

It is to be understood that various changes in shape, size and arrangement of the elements of this invention as claimed may be resorted to in actual practice, if desired.

Having thus described the invention, what is claimed as new and to be secured by Letters Patent is:

1. A device for controlling the duration of a pre-set timed period in which a predetermined amount of gas mixture containing dry oxygen is delivered to a patient during inhalation and exhalation cycling, respectively, from the outlet tube of a respirator unit to a patient, said device fitted with means to permit said predetermined amount of gas mixture containing dry oxygen to flow from the respirator unit during inhalation cycling and exhalation cycling, respectively, to the patient for said pre-set timed period, and upon termination of said pre-set timed period, said means acting to shut off the flow of said dry oxygen gas mixture to the patient and substitute a flow of air from the atmosphere to the patient at the conclusion of said pre-set timed period, comprising a housing fitted with a first inlet tube with means on said inlet tube to detachably engage the outlet tube of a respirator in a sealed engagement, said housing fitted with a second inlet tube leading from a source of atmospheric air, valve means in said housing, said first and second inlet tubes each joined in the housing to said valve means, an outlet tube in said housing, said valve means is also connected to said outlet tube of the housing, said outlet tube of the housing fitted with means to detachably join a tube that may be employed to connect to a face mask secured to a patient for supply of the dry oxygen gas mixture from the respirator unit, said valve means being moveable from a first position in which the housing outlet tube is connected only to the first inlet tube, to a second position in which the housing outlet tube is connected only to the second inlet tube, with a timer device mounted to said housing means to manually actuate said timer device and initiate said pre-set timed period, said timer device is fitted with means to cause the valve to move from the said first position to the said second position, at the conclusion of said pre-set timed period of time after the timer device has been manually actuated.

2. The invention as recited in claim 1 further including filter means in said second inlet.

3. The invention as recited in claim 1 including manual means for actuating said valve means.

4. The combination as recited in claim 1 in which the timer device is fitted with alarm means which are actuated at the conclusion of the pre-set time period substantially simultaneously with the movement of the valve to the first position, and the joining of the outlet tube to the device to the inlet tube leading to a source of atmospheric air.

5. The combination as recited in claim 1 in which the timer is fitted with adjustable means to regulate the duration of the pre-set period of time.

6. The combination as recited in claim 1 in which the timer device is fitted with means to cause the valve to move from the first position to the second position when the timer device is initially manually actuated.

7. The combination as recited in claim 1 in which the means to cause the valve means to move include an electric motor linked to the valve means and switch means responsive to the timer device for actuating said electric motor at the termination of said timed period to move said valve means from its first position to its second position.

8. The combination as recited in claim 1 together with a respirator unit joined to the first inlet tube of the device.

\* \* \* \* \*